(12) United States Patent
Irisawa (10) Patent No.: US 7,740,408 B2
(45) Date of Patent: Jun. 22, 2010

(54) COUPLING DEVICE, AUXILIARY DEVICE AND ADAPTOR FIXING MEMBER

(75) Inventor: Yuichiro Irisawa, Ashigarakami-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

(21) Appl. No.: 12/391,645

(22) Filed: Feb. 24, 2009

(65) Prior Publication Data
US 2009/0196554 A1 Aug. 6, 2009

Related U.S. Application Data

(63) Continuation of application No. PCT/JP2007/066297, filed on Aug. 22, 2007.

(30) Foreign Application Priority Data
Aug. 24, 2006 (JP) .............................. 2006-228323

(51) Int. Cl.
G02B 6/38 (2006.01)
(52) U.S. Cl. .............................. 385/66; 385/83; 385/84
(58) Field of Classification Search .................. 385/53, 385/55, 66, 83, 84
See application file for complete search history.

(56) References Cited

U.S. PATENT DOCUMENTS 4,898,446 A * 2/1990 Hinckley ...................... 385/72
5,005,940 A * 4/1991 Modrey ........................ 385/55
6,179,482 B1 * 1/2001 Takizawa et al. ............. 385/81
6,409,391 B1 * 6/2002 Chang .......................... 385/53
2006/0093300 A1 * 5/2006 Marrs et al. ................. 385/134

FOREIGN PATENT DOCUMENTS

| JP | 4-091315 U | 8/1992 |
| JP | 2001-507251 A | 6/2001 |
| JP | 2005-533533 A | 11/2005 |
| WO | WO 98/23984 A2 | 6/1998 |
| WO | WO 03/088826 A1 | 10/2003 |

OTHER PUBLICATIONS

Form-PCT/ISA/210 (International Search Report) dated Sep. 18, 2007.
English-Language Translation of International Preliminary Report on Patentability (Forms PCT/IB/338 and PCT/IPEA/409) mailed Mar. 12, 2009 in PCT/JP2007/066297, The International Bureau of WIPO, Geneva, CH.

* cited by examiner

*Primary Examiner*—Daniel Petkovsek
(74) *Attorney, Agent, or Firm*—Buchanan Ingersoll & Rooney PC (57) ABSTRACT

A coupling device for coupling optical fiber cables facilitates positioning in a circumferential direction for coupling a connector. When a connector fixing member is inserted into an adaptor fixing member, a protruding section of the connector fixing member slides along an end surface of the adaptor fixing member, and is automatically guided to a notched section.

8 Claims, 10 Drawing Sheets

COUPLING DEVICE, AUXILIARY DEVICE AND ADAPTOR FIXING MEMBER

This application is a continuation of International Application No. PCT/JP2007/066297 filed on Aug. 22, 2007, the entire content of which is incorporated herein. This application also claims priority to Japanese Application No. 2006-228323 filed on Aug. 24, 2006, the entire content of which is incorporated herein by reference.

TECHNICAL FIELD

The disclosed subject matter relates to a coupling device for coupling optical fiber cables, and component members of such cables. More specifically, the disclosed subject matter pertains to a coupling device for coupling optical fibers in a medical diagnostic apparatus.

BACKGROUND DISCUSSION

In recent years, with the progress of high-capacity communication and the like, there has been an increasing demand for optical-fiber connectors as coupling devices for coupling optical fiber cables, in the field of communication and the surrounding fields. Practical examples of the optical-fiber connectors include FC connectors, SC connectors and MU connectors.

These connectors are each provided with a mechanism for avoiding relative turning of optical fiber cables, so as to prevent end portions (contact surfaces) of the coupled optical fiber cables from injuring each other. For example, in the case of the FC connectors, turning in the circumferential direction. is avoided by a, pin and a groove, whereas in the cases of the SC connectors and MU connectors, turning in the circumferential direction is avoided by utilizing the shapes of the connectors. Examples are disclosed in JP-T-2005-533533 and JP-T-2001-507251.

The presence of such a mechanism causes the user to perform positioning in the circumferential direction at the time of coupling the connectors. Particularly, in the case of the connectors of the APC type in which inclination angles are provided at end portions of optical fiber cables in order to suppress reflection noises, positioning with higher accuracy is demanded.

In recent years, in the medical fields also, various medical apparatus have been employed which utilize light such as optical coherent tomography diagnostic apparatus (OCT). These medical apparatus utilize light as a signal, and transmission of the signal is performed by use of an optical fiber cable. Therefore, use of optical-fiber connectors for coupling optical fiber cables is indispensable to these apparatus.

In the medical field, medical personnel oftentimes wear protective garments including rubber gloves. In a situation where the user has to couple a connector while wearing rubber gloves, positioning in the circumferential direction is not easy to perform. Also, when the optical fiber cable is touched by a stained hand, correct transmission of a signal may be difficult, if not impossible. Therefore, it is desirable to preliminarily protect the connector by use of a protective cover or the like, at the time of coupling the connector. In such a case, the positioning in the circumferential direction can become more difficult to perform.

SUMMARY

A coupling device for coupling optical fiber cables includes a first fixing member and a second fixing member. The first fixing member is comprised of a wall defining a cylindrical first hollow shape in which a first coupling terminal is disposed, wherein the cylindrical first hollow shape possesses an open end portion at one end of the cylindrical first hollow shape. The second fixing member comprises a wall defining a cylindrical second hollow shape in which a second coupling terminal is disposed. The second fixing member is slidably positionable inside the first fixing member, during which the outer surface of the wall of the second fixing member faces the inner surface of the wall of the first fixing member. The first fixing member comprises, at the open end portion, a notched section extending in the axial direction of the cylindrical first hollow shape, with the open end portion of the first fixing member including an inclined end surface having an inclination angle which extends toward the open end side in the axial direction of the hollow section, with an open end of the notched section as a center. The outer surface of the wall of the second fixing member comprises a protruding portion extending in a longitudinal direction of extent of the second fixing member. The inclined end surface of the first fixing member possesses spiral shapes with respect to clockwise and counterclockwise circumferential directions, with the open end of the notched section as a center. The protruding section of the second fixing member contacts the inclined end surface of the first fixing member during insertion of the second fixing member into the first fixing member, and the protruding section slides on the inclined end surface to be guided to the notched section in response to urging of the second fixing member further in an insertion direction.

The coupling device here facilitates the positioning in the circumferential direction (rotational positioning) for coupling a connector, in a coupling device for coupling optical fiber cables.

BRIEF DESCRIPTION OF DRAWING FIGURES

Additional details and features of the device and apparatus disclosed here will become more apparent from the detailed description below considered with references to the accompanying drawing figures which are briefly described next.

DETAILED DESCRIPTION

Embodiments of the coupling device and apparatus are described below in detail. In each of the following embodiments, the coupling device is described as being applied to an optical coherent tomography diagnostic apparatus (OCT), though the use of the coupling device is not limited in this regard. The coupling device has useful application in other medical devices and may also be used with devices other than medical devices.

1. Optical Coherent Tomography Diagnostic Apparatus

Figure 1:
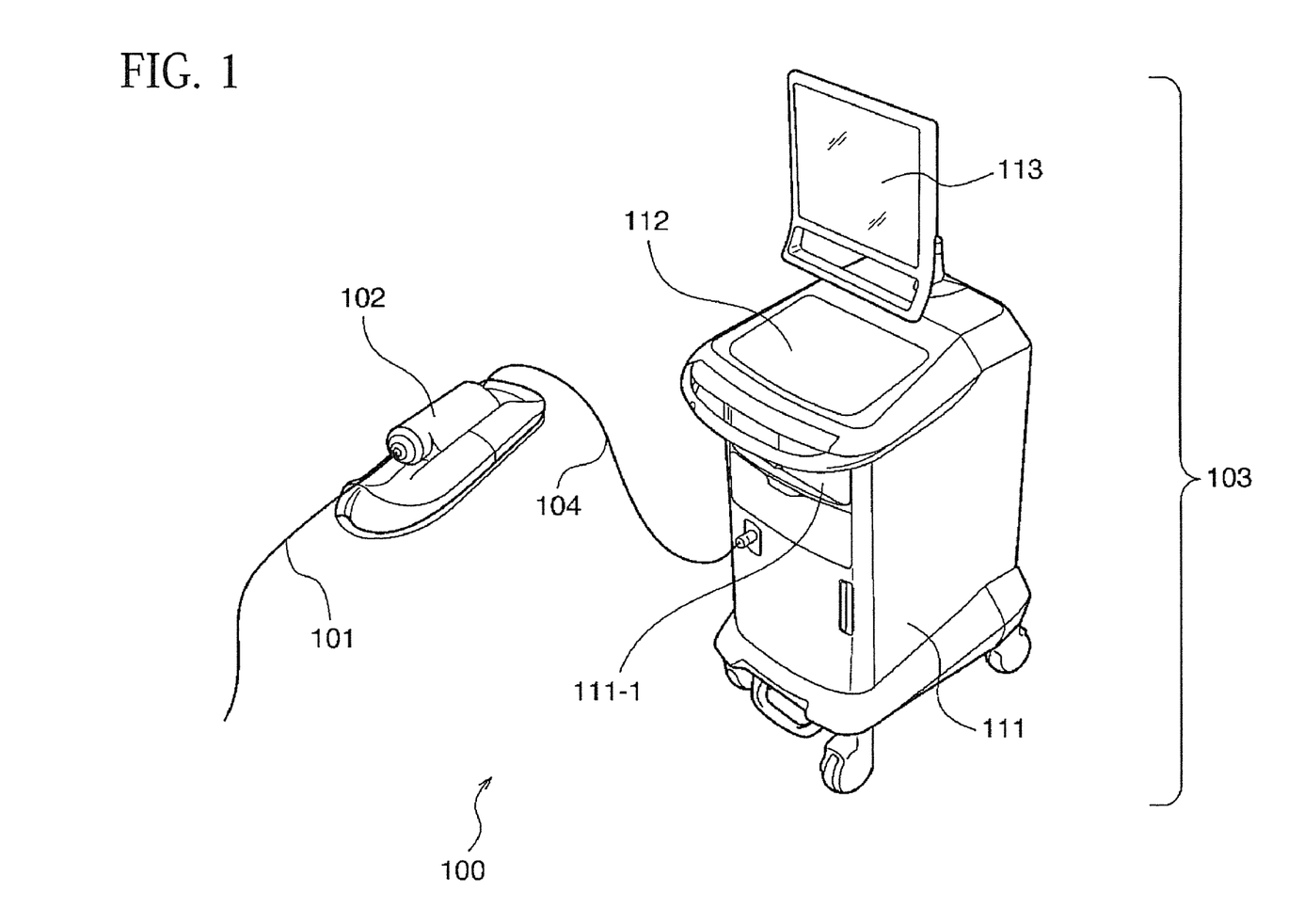
FIG. 1 is a perspective view of an optical coherent tomography diagnostic apparatus.

FIG. 1 shows an example of an optical coherent tomography diagnostic apparatus 100 to which the coupling device disclosed here has useful application. As shown in FIG. 1, the optical coherent tomography diagnostic apparatus 100 includes a catheter section 101, a scanner/pull-back section 102, and an operation control device 103, with the scanner/pull-back section 102 and the operation control device 103 being connected to each other by a signal cable 104. The catheter section 101 is inserted directly into a patient's blood vessel, and measures the states inside the blood vessel by use of low-coherent light radiated from a distal portion of the blood vessel. The scanner/pull-back section 102 determines radial scanning of an imaging core 220 in the catheter section 101.

The operation control device 103 permits the inputting of various set points to perform optical coherent tomography diagnosis, and also operates to process the data, obtained upon measuring and displaying the processed data in the form of cross-sectional images.

The operation control device 103 includes a main control unit 111 which processes the data obtained through measurement and outputs the results of the processing. The operation control device 103 also includes a printer/DVD recorder 111-1 which prints the results of the processing conducted in the main control unit 111 and stores the results as data.

The operation control device 103 further includes a console panel 112 at which the user inputs various set points, and a liquid crystal display 113 which displays the results of the processing performed in the main control unit 111.

2. Catheter Section 101

2.1 General Configuration of Catheter Section 101

Figure 2:
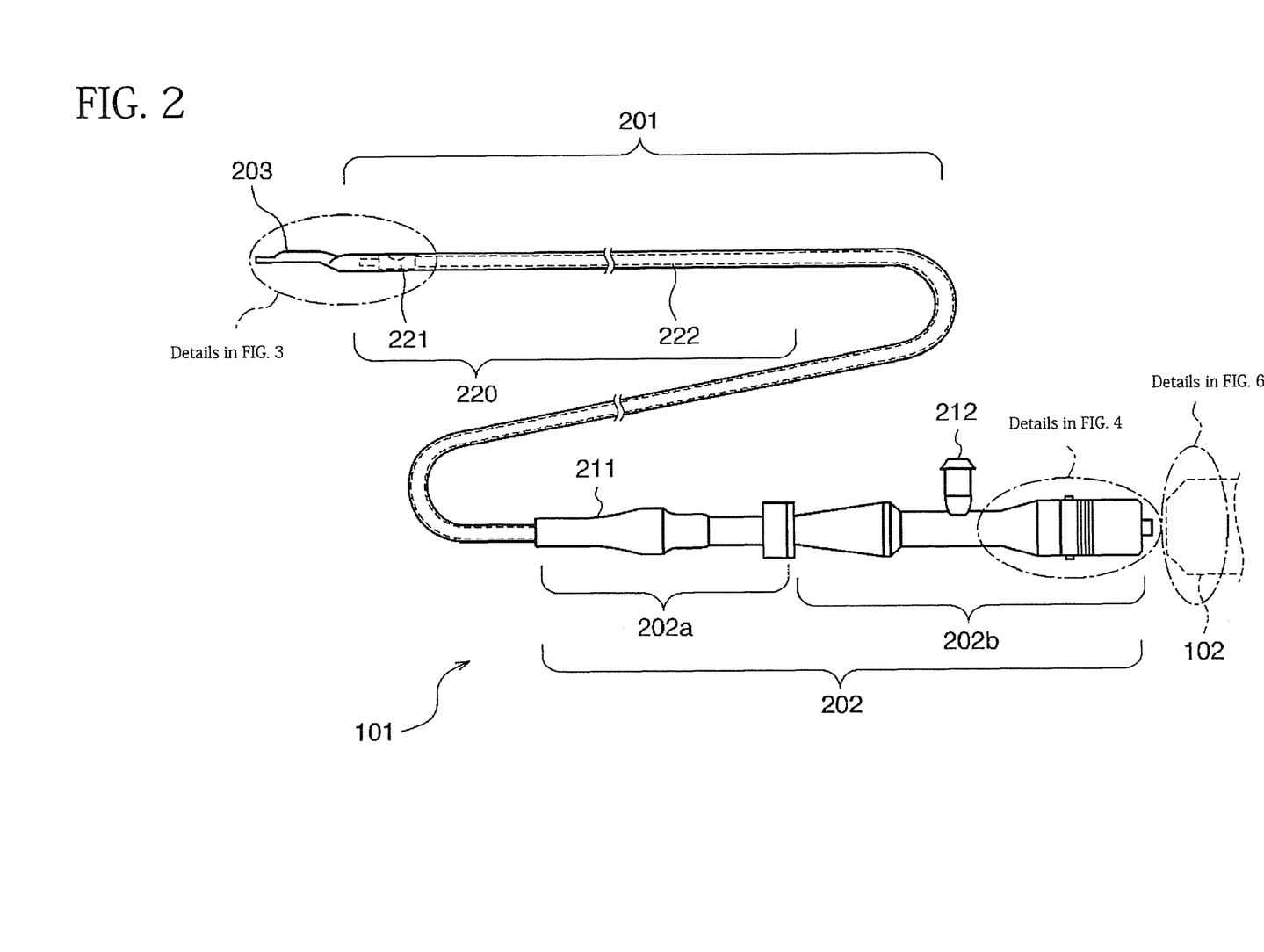
FIG. 2 is a side view of a catheter section.
Figure 3:
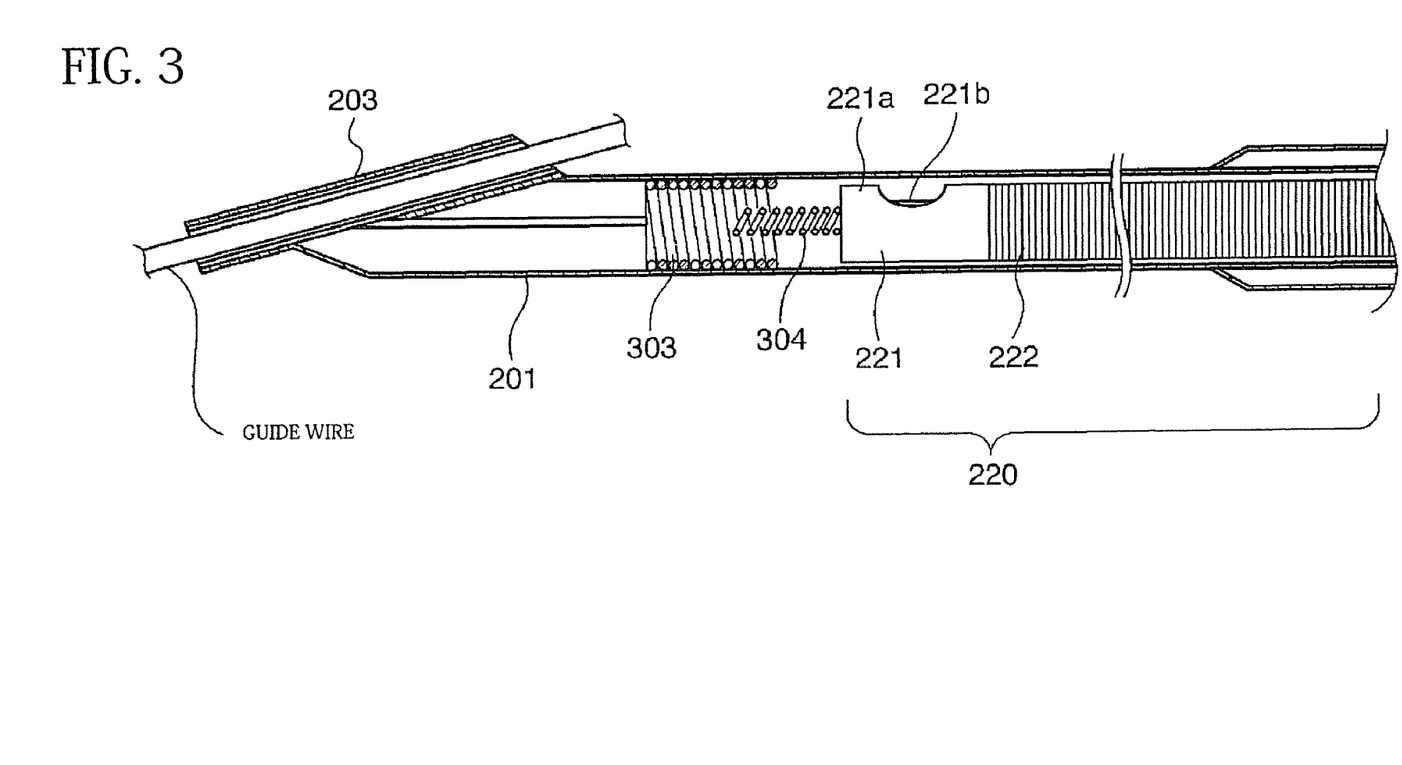
FIG. 3 is a cross-sectional view of a distal portion of the catheter section.

The general configuration of the catheter section 101 is illustrated in FIG. 2. As illustrated, the catheter section 101 includes an elongated catheter sheath 201 sized and configured to be inserted into or positioned in a blood vessel, and a connector section 202 not inserted into a blood vessel but disposed on the user's hand side to be operated by the user. The distal end of the catheter sheath 201 includes a guide wire lumen 203. The catheter sheath 201 is formed with a lumen which is continuous over the range from a portion coupled with the guide wire lumen 203 to a portion coupled with the connector section 202. Details associated with portions of the catheter are shown in FIG. 3.

The catheter section includes an imaging core 220 including a light irradiation end 221 for transmitting and receiving measuring light, and a drive shaft 222 for transmitting a driving force to rotate the light irradiation end 221. The drive shaft 222 is positioned in the lumen of the catheter sheath 201 and extends over substantially the entire length of the catheter sheath 201.

The connector section 202 includes a sheath connector 202a configured to be integrated (e.g., attached or fixed) with the proximal end of the catheter sheath 201, and a drive shaft connector 202b configured to be integrated (e.g., fixed or attached) with the proximal end of the drive shaft 222.

An anti-kinking protector 211 is provided, at a boundary portion between the sheath connector 202a and the catheter sheath 201, whereby a predetermined rigidity is maintained and sharp bending (kinking) can be inhibited or prevented from occurring due to an abrupt change.

Figure 4:
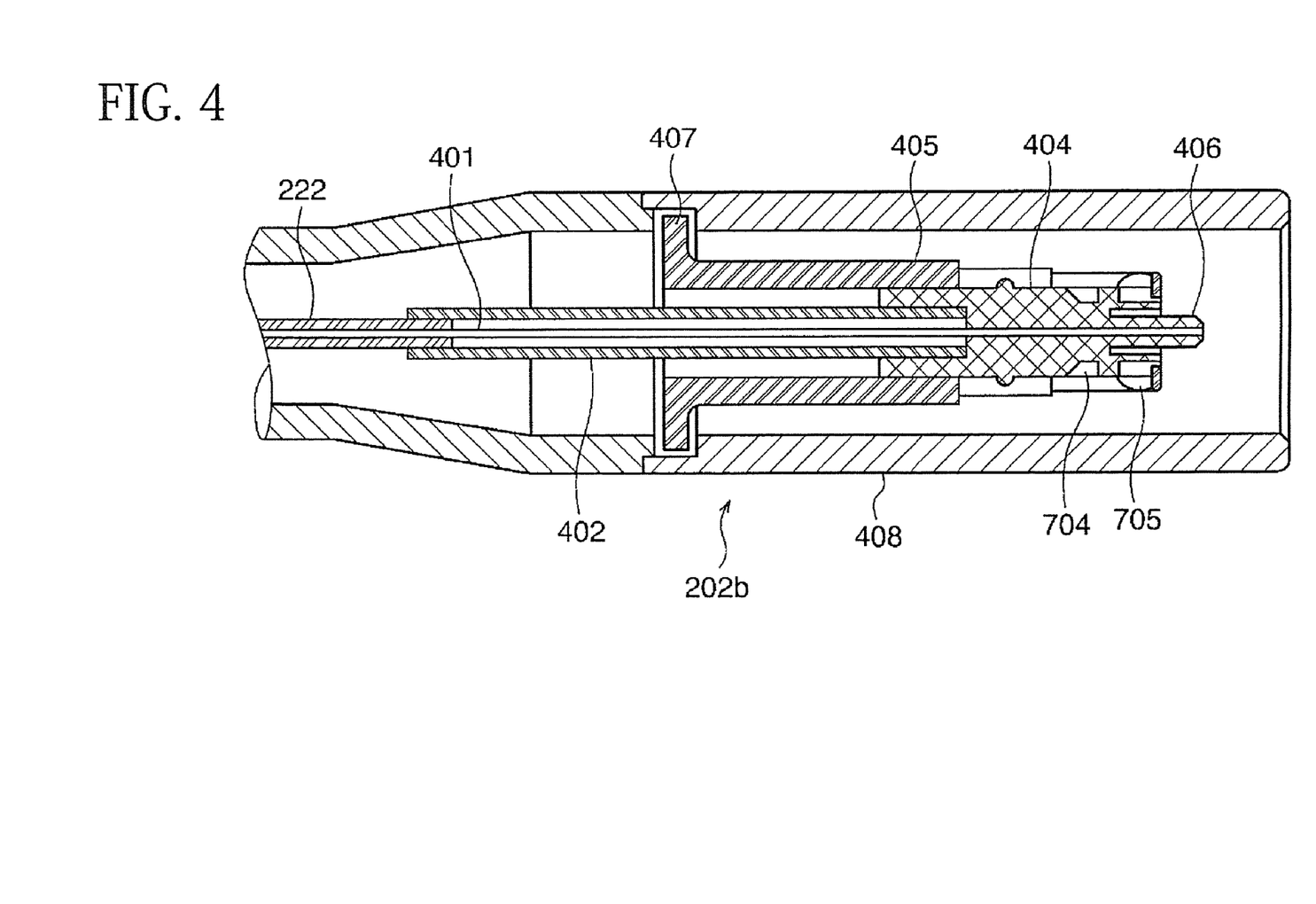
FIG. 4 is a cross-sectional view of the internal configuration of a drive shaft connector.
Figure 6:
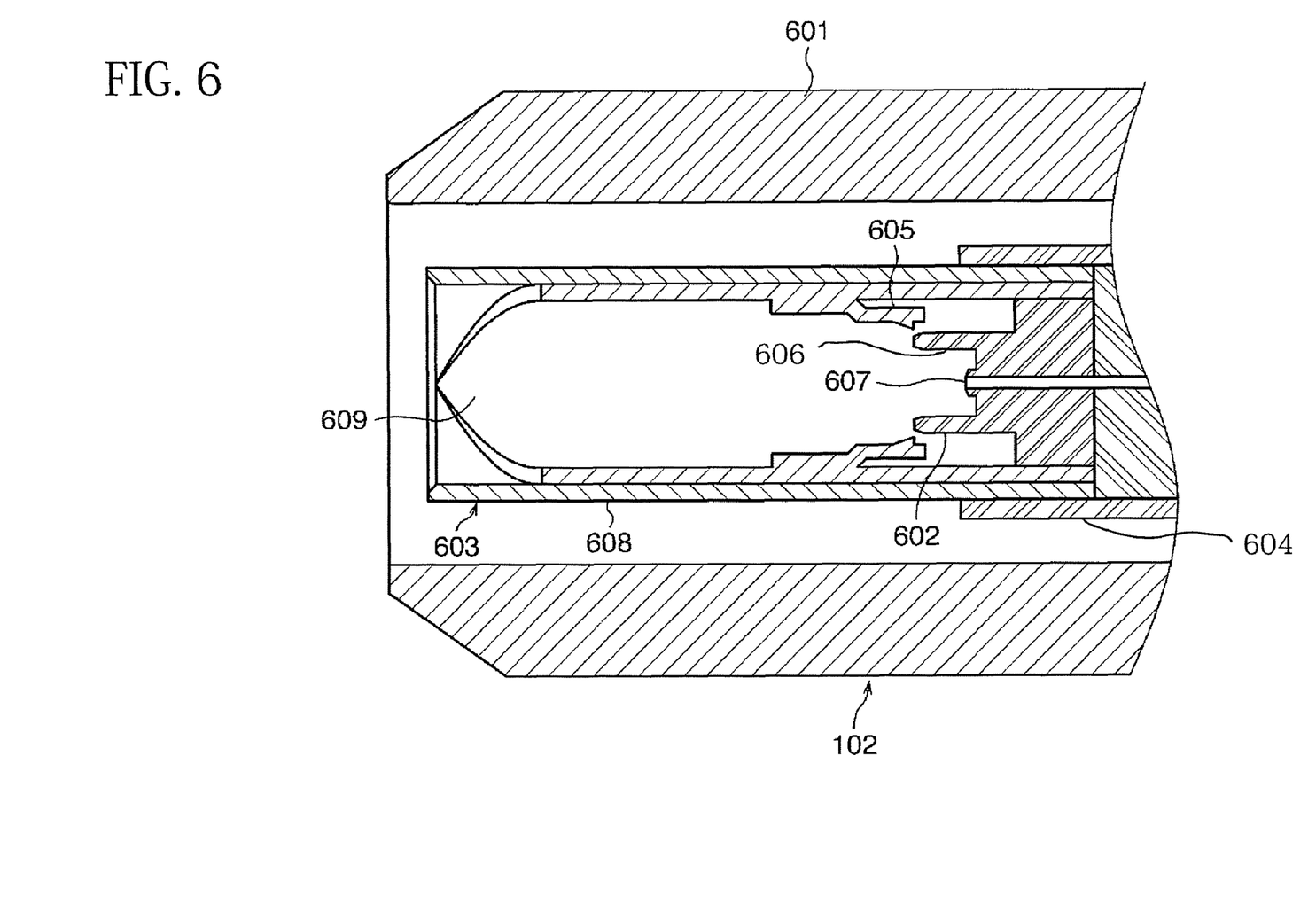
FIG. 6 is a cross-sectional view of the internal configuration (on the side for connection to the proximal end of the drive shaft connector) of a, scanner/pull-back section forming a part of the optical coherent tomography diagnostic apparatus.

The proximal end of the drive shaft connector 202, details of which are shown in FIG. 4, is configured to be coupled to the scanner/pull-back section 102. Features associated with the scanner/pull-back section 102 are shown in FIG. 6 and will be described below. The coupling device disclosed here is applied to the coupling of optical fiber cables between the proximal end of the drive shaft connector 202b and the scanner/pull-back section 102.

2.2 Configuration of Catheter Section Distal Portion

Referring to FIG. 3, the distal portion of the catheter section 101 includes the light irradiation end 221 provided with a prism or mirror 221b, by which light guided through an optical fiber is radiated sideways, and a housing 221a holding the prism or mirror 221b. The measuring light is radiated toward tissues inside a body lumen by the prism or mirror 221b, and the reflected light from the tissues inside the body lumen is received by the prism or mirror 221b.

The drive shaft 222 is coil-shaped, with an optical fiber disposed in the coiled drive shaft, and extends from the light irradiation end 221 to the connector section 202.

The prism or mirror 221b is positioned inside the housing 221a. The housing 221a is connected to the drive shaft 222 on the proximal side of the drive shaft. In addition, the distal side of the housing 221a is provided with a short coil-shaped elastic member 304.

The elastic member 304 is coil-shaped and made of a stainless steel wire. Disposing the elastic member 304 on the distal side enhances the stability at the time of rotation of the imaging core 220.

A radiopaque coil 303 is fixed to the inner surface of the catheter lumen to permit confirmation of the position of a distal portion of the catheter sheath 201 in the body.

The guide wire lumen 203 is a lumen sized and configured to receive a guide wire. The guide wire lumen 203 is used to guide the catheter sheath 201 along a guide wire, wherein the guide wire is preliminarily inserted in a body lumen to a diseased portion.

The drive shaft 222 includes, for example, a multi-turn multi-layer firm-contact coil or the like, of a stainless steel or other metallic wire which is rotatable and slidable relative to the catheter sheath 201, is flexible and has characteristics permitting successful transmission of rotation.

2.3 Configuration of Drive Shaft Connector

FIG. 4 illustrates the internal configuration of the proximal end of the drive shaft connector 202b. As shown in FIG. 4, an optical fiber connector (second coupling terminal) 404, which is a connector for optical fiber, is disposed at the proximal end of the drive shaft connector 202b. The optical fiber connector 404 allows the optical fiber cable 401 to be optically coupled to an optical fiber cable in the scanner/pull-back section 102.

The optical fiber connector 404 is joined to the drive shaft 222 through a joint pipe 402. In addition, the connector 404 is disposed in the inside of a connector fixing member (second fixing member) 405 having a hollow cylindrical shape. The connector fixing member 405 possesses a wall defining the cylindrical hollow shape or section. The connector 404 holds and fixes an end portion of the optical fiber cable 401 provided with a ferrule 406 at the tip of the optical fiber cable 401. The end portion of the optical fiber cable 401 is processed to be of the APC type formed with an inclination angle against the traveling direction of light, in order to prevent noises from being generated due to reflection of light at an end surface. The distal end portion of the connector fixing member 405 has a circular disk-shaped flange 407, and is rotatably retained in the inside of a housing 408 of the drive shaft connector 202b. The housing 408 serves as a protective cover.

The connector fixing member 405 positions the connector 404 in a circumferential direction in cooperation with a first fixing member at the time of connection with a first coupling terminal which will be described later. For convenience, the terminal on the catheter section side is referred to as the "connector" and the terminal on the other side is referred to as the "adaptor." In the following description, the connector 404 and the connector fixing member 405 are together referred to as a connector device.

2.4 Configuration of Optical Fiber Cable

Figure 5:
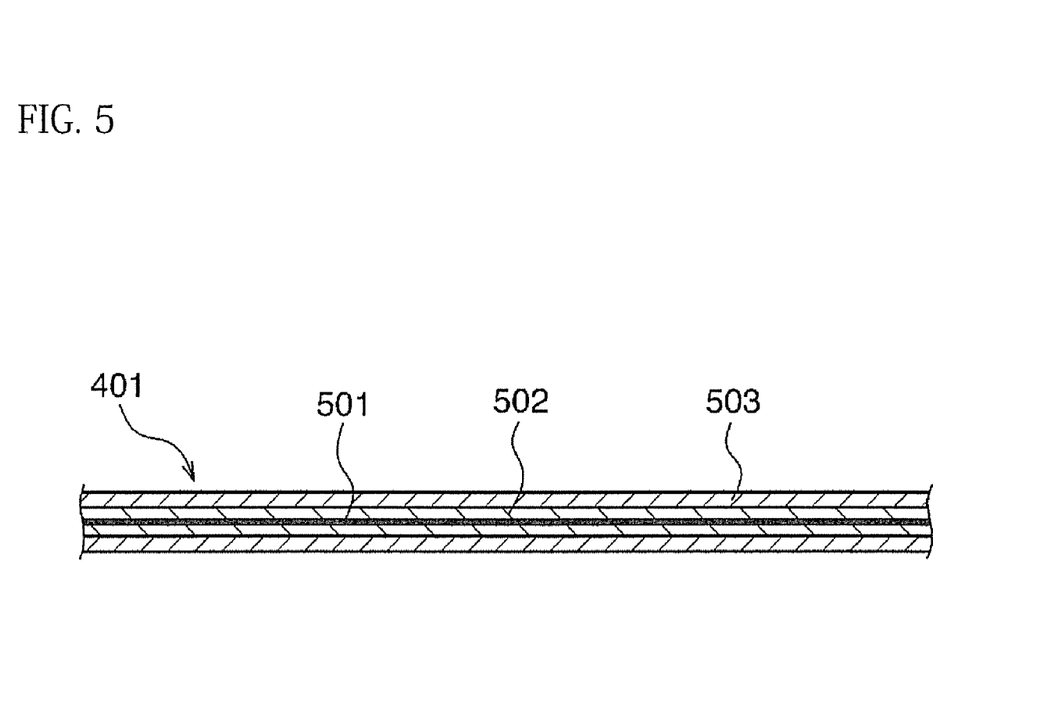
FIG. 5 is a cross-sectional view of an optical fiber.

FIG. 5 illustrates the general configuration of a single-mode optical fiber cable. The optical fiber cable 401 includes a core 501 for transmitting light, and a clad 502 surrounding the core and having a refractive index slightly lower than that of the core 501. Light is transmitted through total reflection repeated at the boundary surface between the core 501 and the clad 502 only in the case where the angle of incidence is greater than the critical angle. In addition, the outer surface of the clad 502 of the optical fiber 401 is covered with a resin material, called jacket 503, so that even when the optical fiber 401 is bent with a great curvature, stress is dispersed and the optical fiber 401 is inhibited or prevented from breaking.

3. Internal Configuration of Scanner/Pull-back Section

FIG. 6 shows the internal configuration of the scanner/pull-back section 102, on the distal side that is adapted to be connected to the proximal end of the drive shaft connector 202b. As shown in FIG. 6, the scanner/pull-back section 102 includes a housing 601. The housing 408 of the drive shaft connector 202b is fitted into the inner surface of the housing 601. Positioned inside the housing 601 is an adaptor 602 constituting a first coupling terminal that is to be coupled with the connector 404 of the drive shaft connector 202b. The interior of the housing 601 is also outfitted with an adaptor fixing member 603 constituting a first fixing member. The adaptor fixing member 603 has a hollow cylindrical shape. The adaptor 602 is fixed in the inside of the adaptor fixing member 603 in a relatively non-rotatable manner. The adaptor fixing member 603 positions the connector 404 in the circumferential direction in cooperation with the connector fixing member 405 at the time of coupling with the connector 404. The adaptor fixing member 603 is joined to a driving force relay pipe 604 for relaying a driving force of a rotational drive unit (motor), whereby after coupling with the connector 404, the rotational drive of the driving force relay pipe 604 is transmitted to the drive shaft 222.

The inner surface of the adaptor fixing member 603 is provided with a pair of claws 605. The claws 605 are configured, and adapted to engage the connector 404 so as to firmly unify the connector 404 and the adaptor 602. The adaptor 602 is provided with a hole 606 of a female-type structure for receiving the ferrule 406 of the connector 404, and an optical fiber end portion 607 processed to be of the APC type is fixed at the bottom of the hole 606. An end portion opposite the optical fiber end portion 607 is connected to a light source.

In addition, the adaptor fixing member 603 includes a protective tube 608 which determines an outer surface, and a main body 609 which is fixed to the inner surface of the protective tube 608 and which determines or defines the inner surface of the adaptor fixing member 603.

In the following description, the adaptor 602 and the adaptor fixing member 603 together will be referred to as the adaptor device. In short, the coupling device includes the connector device and the adaptor device which have structures or configurations allowing them to be coupled together.

4. Configuration of Coupling Device

A coupling device according to one disclosed embodiment will be described below.

4.1 Configuration of Connector Device

Figure 7A:
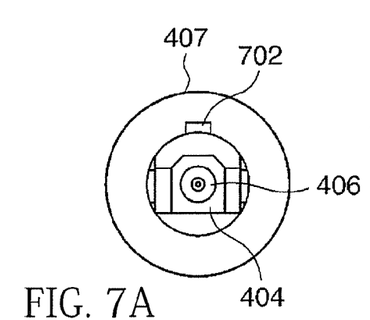
FIG. 7A is a end view of a connector device.
Figure 7B:
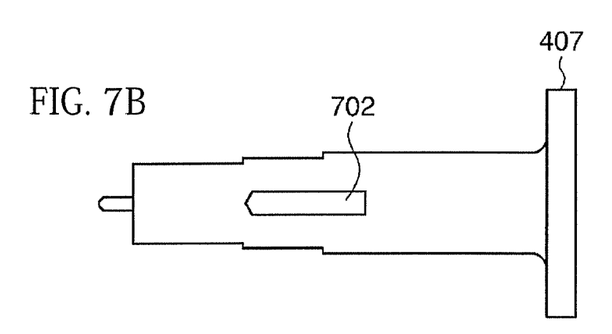
FIG. 7B is a side view of the connector device.
Figure 7C:
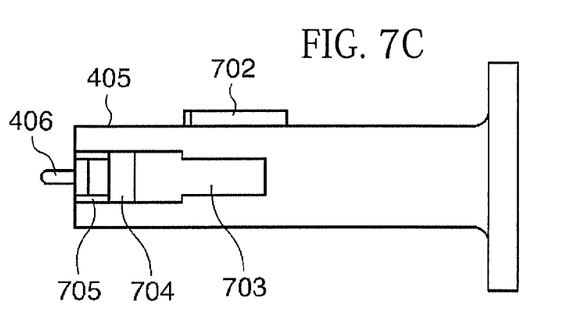
FIG. 7C is a top view of the connector device.
Figure 7D:
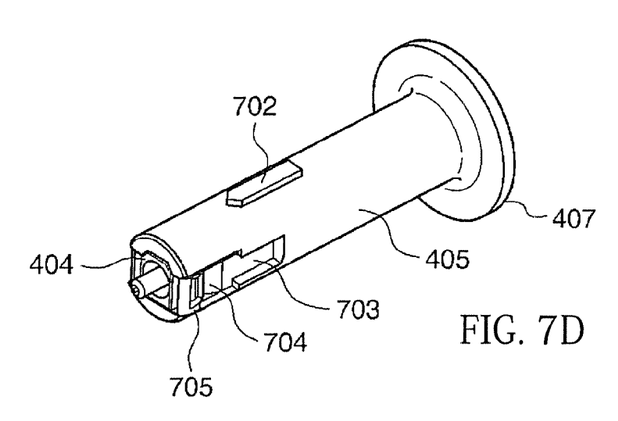
FIG. 7D is a perspective view of a connector device.

FIGS. 7A-7D illustrate the connector device. As shown in FIG. 7A, the connector device includes the connector fixing member 405 having a hollow cylindrical shape, and the connector 404 disposed inside the connector fixing member 405. A ferrule 406 is formed at the end portion of the connector 404.

In addition, as shown in FIGS. 7A-7D, the outer cylindrical wall of the connector fixing member 405 includes an outer wall portion 702 which, as described below in more detail, is adapted to engage and slide along a wall surface of the adaptor fixing member 603. In the illustrated embodiment, this outer wall portion 702 of the connector fixing member 405 is in the form of a protruding section 702 provided on the outer peripheral surface of the connector fixing member 405. The protruding section 702 extends in the longitudinal direction. The proximal side end portion of the protruding section 702 is a pointed end that reduces the contact resistance with the end surface of the adaptor fixing member 603 which will be described later. The connector fixing member 405 has an outer diameter R dimensioned to ensure that the outer peripheral surface of the connector fixing member 405 is slidable relative to the inner wall surface of the adaptor fixing member 603 when the connector fixing member 405 is inserted into the hollow section of the adaptor fixing member 603.

In addition, the connector fixing member 405 includes a pair of slits 703 in left-right symmetry at positions circumferentially spaced from the protruding section 702. That is, the slits 703 are positioned diametrically opposite one another on the connector fixing member 405. The slits 703 penetrate the wall of the connector fixing member 405 (i.e., extend completely through the cylindrical wall of the connector fixing member 405). The side surface of the connector 404 are exposed at the slits 703, and a recessed section 704 for engagement with the claws 605 of the adaptor fixing member 603 is positioned at each of the two exposed portions.

When the connector 404, the adaptor 602 and the adaptor fixing member 603 are unified by engagement of the claws 605 with the recessed sections 704, the connector fixing member 405 is not necessarily limited by the connection of both of them, so that the connector fixing member 405 is somewhat slidable to the front and rear sides along the axial direction. To detach or disconnect the connector 404 and the adaptor 602 which have previously been coupled to each other, the user grips the housing 408 of the drive shaft connector 202b and pulls it off, whereupon the connector fixing member 405 is slid in the pulling-off direction through the flange 407. In this situation, rounded projections 705 at proximal portions of the slits 703 push the claws 605 wider, thereby disengaging the claws 605 from the recessed sections 704 so that the connector 404 can be pulled off and separated from the adaptor 602.

4.2 Adaptor Device

Figure 8A:
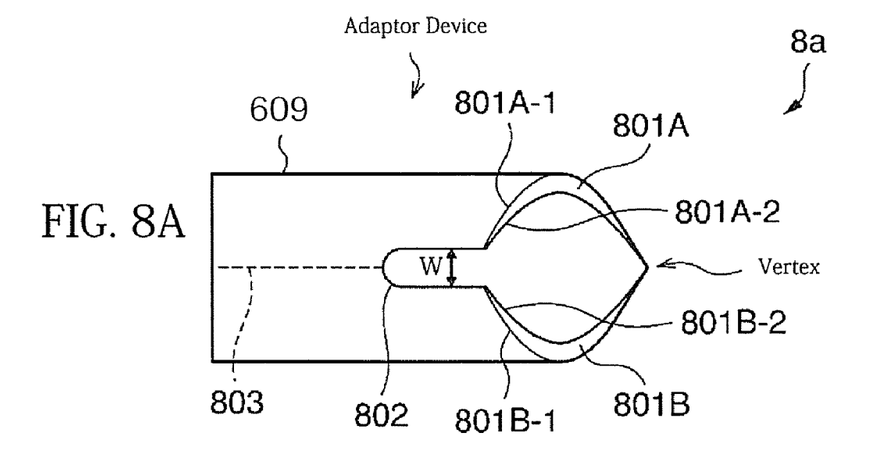
FIG. 8A is a perspective view of an adaptor device.
Figure 8B:
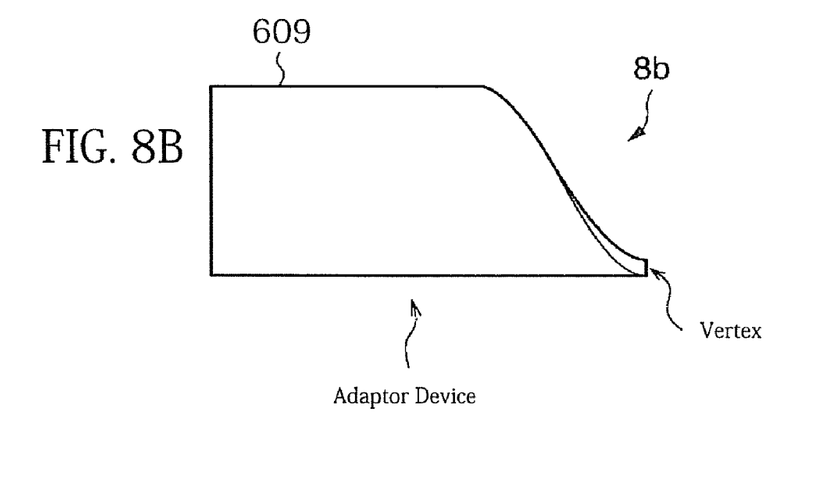
FIG. 8B is a side view of an adaptor device.
Figure 8C:
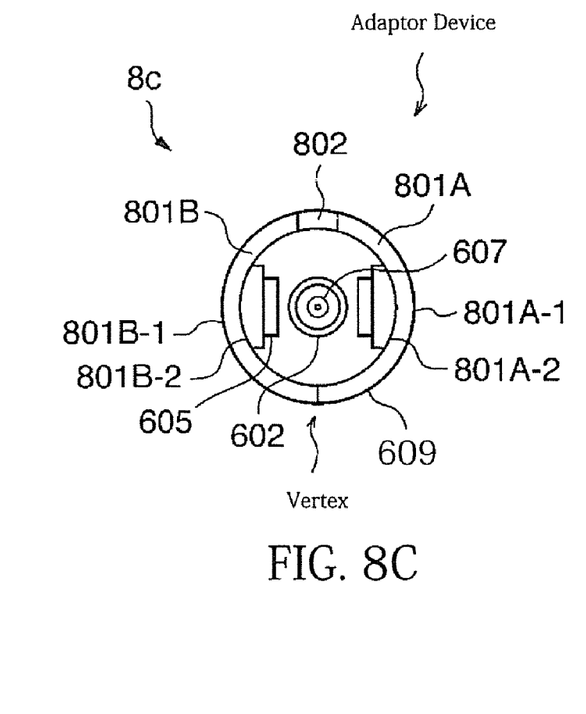
FIG. 8C is a end view of an adaptor device.

FIGS. 8A-8C illustrate the main body 609 of the adaptor device. As described above, the adaptor device includes the adaptor fixing member 603 having a hollow cylindrical shape, and the adaptor 602 fixed in the inside of the adaptor fixing member 603. The adaptor fixing member 603 includes the protective tube 608 and the main body 609. For illustration of the structure of the main body 609, the main body 609 is shown by itself in FIGS. 8A-8C.

The main body 609 is a cylindrical hollow section possessing a wall defining the cylindrical hollow shape or section. The protective tube 608 is provided for the purpose of covering a pointed distal end of the main body 609, thereby preventing injury of the user and/or breakage of the connector 404 from occurring, and serving as a guide for insertion of the fixing member 405 into the main body 609. The protective tube 608 and the main body 609 may be molded integrally. As shown in FIG. 8A, the open side of the main body 609 is provided with end surfaces 801A and 801B forming an inclined end surface, or forming respective inclined end surfaces. As can be understood from the FIG. 8A illustration, the inclined end surface defined by the end surfaces 801A and 801B possesses a distal-most end or vertex (i.e., the right-most end of the inclined surface in FIG. 8A) and an oppositely located proximal-most end (i.e., the left-most end of the inclined surface in FIG. 8A).

In addition, as shown in FIG. 8A, a notched section 802 extending in the longitudinal direction of the main body 609 (in the axial direction of the hollow section forming the main body 609) extends from a part of the end surfaces 801A, 801B of the main body 609. The notched section 802 has a width w in the circumferential direction. The width w of the notched section 802 is dimensioned so that the protruding section 702 of the connector fixing member 405 will fit in the notched section 802. The notched section 802 possesses an open end opening at the inclined surface, specifically the proximal-most end of the inclined end surface.

As shown in FIG. 8A, the end surface 801A is an end surface extending clockwise along the circumferential direction, starting from the notched section 802, whereas the end surface 801B is an end surface extending counterclockwise along the circumferential direction, starting from the notched section 802. The end surface 801A and the end surface 801B intersect at a position spaced by 180 degrees along the circumferential direction from the notched section 802 (the intersection is referred to below as the vertex). The end surface 801A and the end surface 801B are symmetrical with respect to each other about a plane containing a centerline of the notched section 802 and the vertex.

In addition, the end surface 801A intersects the outer wall surface at an outer wall boundary line 801A-1 which is thus the boundary between the end surface and the outer wall surface. The end surface 801A also intersects the inner wall surface at an inner wall boundary line 801A-2 which is thus the boundary between the end surface and the inner wall surface. Similarly, the end surface 801B intersects the outer wall surface at an outer wall boundary line 801B-1 which is thus the boundary between the end surface 801B and the outer wall surface, while the end surface 801B also intersects the inner wall surface at an inner wall boundary line 801B-2 which is thus the boundary between the end surface 801B and the inner wall surface.

The outer wall boundary line 801A-1, starting from the notched section 802, turningly extends 180 degrees clockwise along the circumferential direction in the manner of forming a spiral shape to intersect with the outer wall boundary line 801B-1 at the vertex. Similarly, the outer wall boundary line 801B-1, starting from the notched section 802, turningly extends 180 degrees counterclockwise along the circumferential direction in the manner of forming a spiral shape to intersect with the outer wall boundary line 801A-1 at the vertex.

Besides, the inner wall boundary line 801A-2, starting from the notched section 802, turningly extends 180 degrees clockwise along the circumferential direction in the manner of forming a spiral shape to intersect with the inner wall boundary line 801B-2 at the vertex. Similarly, the inner wall boundary line 801B-2, starting from the notched section 802, turningly extends 180 degrees counterclockwise along the circumferential direction in the manner of forming a spiral shape to intersect with the inner wall boundary line 801A-2 at the vertex. In this instance, the outer wall boundary line and the inner wall boundary line are equal in pitch of spiral.

Figure 9:
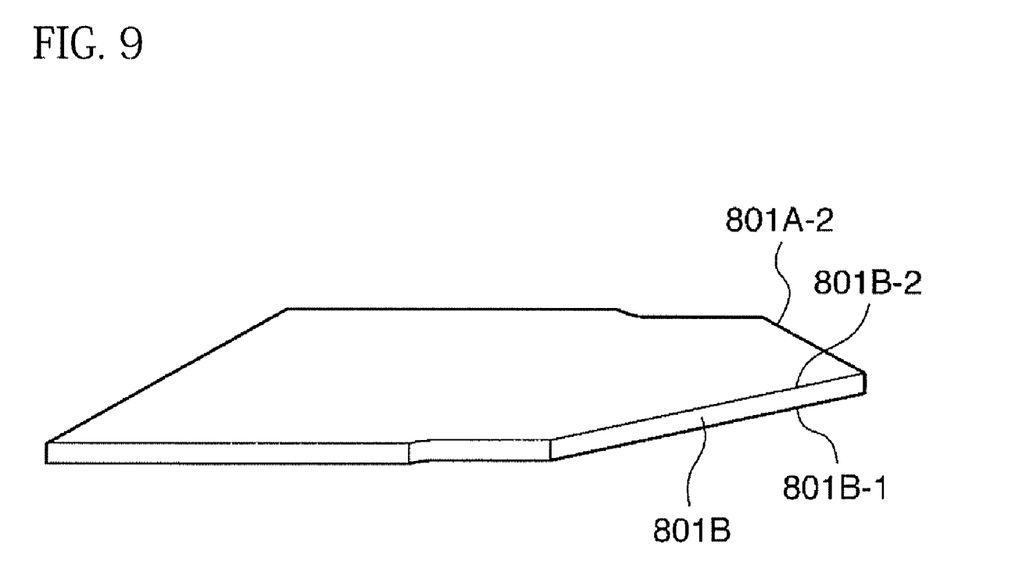
FIG. 9 is a perspective view of an adaptor fixing member.

This shape is also described from another point of view, referring to FIG. 9. When the main body 609 is cut along the dotted line 803 in FIG. 8A, opened up and then flattened-out into a plane, the result is shown in FIG. 9. The dotted line 803 in FIG. 8A lies in a plane containing the centerline of the slot 802 and the central axis of the main body 609. FIG. 9 is the main body 609 cut and flattened-out as described above, with the inner wall side (i.e., the inner surface of the main body 609) up. As shown in FIG. 9, when the main, body 609 is cut and flattened-out into a plane, the inner wall surface and the outer wall surface are parallel to each other (in other words, the material thickness of the main body 609 is constant), while the end surfaces 801A and 801B form surfaces which are perpendicular to the inner wall surface and the outer wall surface. In addition, the inner wall boundary line 801A-2 and the inner wall boundary line 801B-2 are composed of straight lines which are equal in length and angle. Also, the shape of the tip portion (on the inner wall side) of the flattened main body 609 composed of the inner wall boundary line 801A-2 and the inner wall boundary line 801B-2 is an isosceles triangle. Similarly, the shape of the tip portion (on the outer wall side) of the flattened main body 609 composed of the outer wall boundary line 801A-1 and the outer wall boundary line 801B-1 is an isosceles triangle. It should be understood that FIG. 9 is merely a drawing used as a convenience for illustrating the shape of the main body 609, and does not specify or limit the method for producing the main body (adaptor fixing member).

In addition, the shape of the end portion of the main body 609 of the adaptor fixing member 603 is not limited to the spiral structure insofar as it has a structure by which the protruding section 702 of the connector fixing member 405 can be guided into the notched section 802. For example, instead of the end surfaces defined by curved lines always having a constant angle relative to the axial direction, such as a spiral, end surfaces having a fixed inclination angle (end surfaces of a structure as if obtained by skew cutting a hollow cylinder) may also be adopted.

4.3 Operation at the Time of Coupling

Figure 10A:
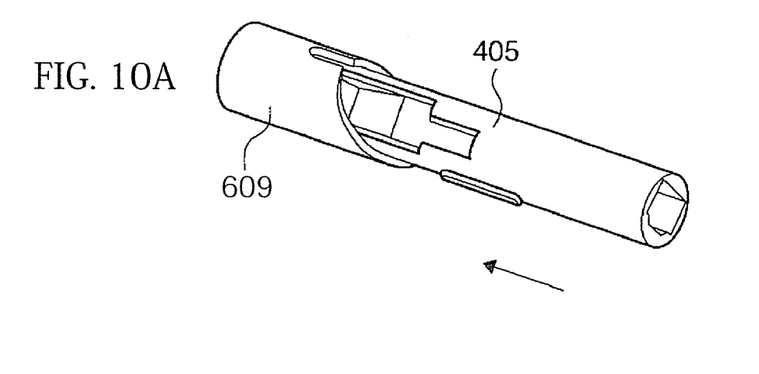
FIG. 10A is a perspective view of a connector fixing member and the adaptor fixing member at the time of coupling a coupling device.

FIGS. 10A-10D show coupling operations associated with coupling together the connector fixing member 405 and the adaptor fixing member 603. In FIGS. 10A-10D, for convenience of description, the drive shaft connector 202b, the housing 601 and the protective tube 608 are omitted. As shown in FIG. 10A, at the time of coupling, while gripping the drive shaft connector (202b), a distal portion of the connector fixing member 405 is inserted into the hollow section of the adaptor fixing member 603 at an arbitrary angle in the circumferential direction (i.e., at an arbitrary rotational orientation). The distal portion of the connector fixing member 405 is inserted into the hollow section of the adaptor fixing member 603 in an insertion direction indicated by the arrow in FIG. 10A.

Figure 10B:
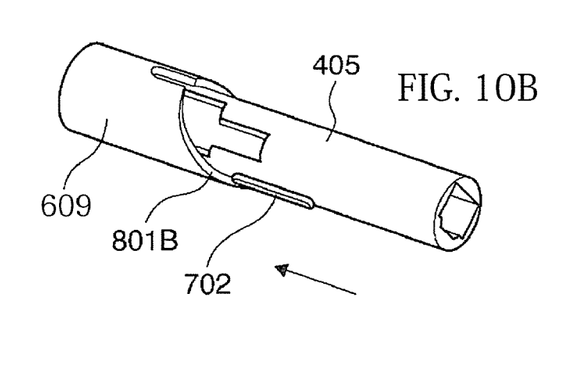
FIG. 10B is a perspective view of the connector fixing member and the adaptor fixing member at a different time during the coupling of the coupling device.

With the connector fixing member 405 pushed further in the insertion direction (the direction of the arrow), the protruding section 702 of the connector fixing member 405 and the end surface 801B of the adaptor fixing member 603 make contact with each other as illustrated in FIG. 10B. When the connector fixing member 405 is urged further in the insertion direction, the protruding section 702 slides along the end surface 801B in the direction of the curved arrow 1001 in FIG. 10C.

Figure 10C:
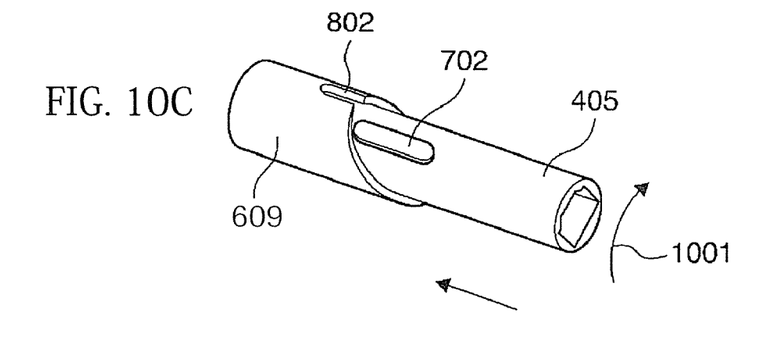
FIG. 10C is a perspective view of the connector fixing member and the adaptor fixing member at a different time during the coupling of the coupling device.

As the protruding section 702 slides along the end surface in the direction of the arrow 1001, the connector fixing member 405 rotates in the circumferential direction in the inside of the drive shaft connector (202*b*).

Figure 10D:
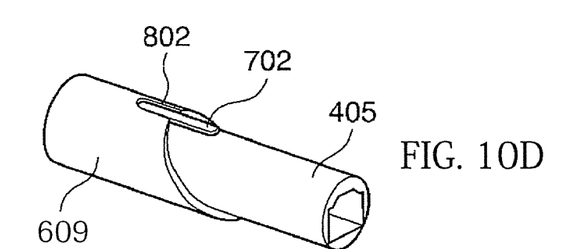
FIG. 10D is a perspective view of the connector fixing member and the adaptor fixing member at a different time during the coupling of the coupling device.

When the connector fixing member 405 is pushed further in the insertion direction, the connector fixing member 405 is further rotated. Thereafter, when the protruding section 702 has reached the position of the notched section 802, the protruding section 702 is fitted into the notched section 802 In short, the protruding section 702 is guided into the notched section 802 solely by pushing the connector fixing member 405 (i.e., solely by applying an axial pushing force between the connector fixing member 405 (drive shaft connector 202*b*) and the main body 609 (adaptor fixing member 603)). Then, upon further pushing in the connector fixing member 405, the protruding section 702 is inserted straight along the notched section 802, whereby the adaptor 602 and the connector 404 are coupled with each other. In short, movement of the connector fixing member 405 in the circumferential direction (i.e., rotational movement of the connector fixing member 405) is restricted (in other words, positioning in the circumferential direction is completed) by fitting the distal end of the protruding section 702 into the notched section 802. In addition, the coupling between the adaptor 602 and the connector 404 is realized by insertion of the protruding section 702 along the notched section 802.

Thus, according to the coupling device of this embodiment, even without strict positioning of the connector 404 in the circumferential direction, if only the distal end of the connector fixing member 405 is inserted into the hollow section of the adaptor fixing member 603, the protruding section 702 is automatically guided toward the notched section 802 following the insertion of the connector fixing member 405, whereby positioning of the connector fixing member 405 at a predetermined angle in the circumferential direction is completed.

As a result, according to this embodiment, positioning in the circumferential direction for coupling connectors in the coupling device for coupling optical fiber cables can be carried out relatively easily. Specifically, the user is required only to move the housing 408 of the drive shaft connector 202*b* rectilinearly in the insertion direction, whereby positioning of the connector fixing member 405 in the circumferential direction (i.e., rotational positioning or orientation of the connector fixing member 405) is automatically performed, and the desired positioning is completed.

In addition, according to the embodiment illustrated and described here, the user does not directly touch the adaptor fixing member 603 (or main body 609) or the connector fixing member 405 with his hand. Therefore, there is little fear of contaminating the end surfaces of the optical fiber cables.

While optical connector terminals of a catheter device are described above in the first embodiment, the disclosure here may also be applied to optical connector terminals for other uses, such as optical communication. In such a second embodiment, it is not necessary to provide any housing for covering a connector fixing member or an adaptor fixing member (such as the housing 408 for the drive shaft connector 202*b* and the housing 601 for the scanner/pull-back section 102 in the first embodiment above). In other words, in this alternative construction, the user grips the connector fixing member directly with his hand. However, since a force is exerted in the direction along which the protruding section 702 is guided along the end surface 801A or 801B, the user can couple the connector and the adaptor to each other at a proper angle or rotational position according to the thus exerted force.

In the first embodiment described above and illustrated in the drawing figures, description has been made of the case where the spiral shapes of the outer wall boundary lines (801A-1, 801B-1) and the inner wall boundary lines (801A-2, 802B-2) are formed between the vertex and the notched section 802 over the whole circumference. However, the disclosure here is not particularly limited to such a case. For example, in a third embodiment, the spiral shapes may be formed at a part or parts between the vertex and the notched section 802. In this case, if the protruding section 702 comes into contact with the end surface 801A or 801B which is not provided with a spiral shape, pushing the connector fixing member 405 would not result in guiding of the protruding section 702 into the notched section 802. In other words, it is necessary for the user to perform positioning in the circumferential direction (i.e., rotational positioning) to such an extent as to bring the protruding section 702 to the end surface 801A or 802B which is provided with a spiral shape. However, even in this case, the work load is reduced remarkably, as compared to the work load in the conventional positioning.

While the disclosure here is presented as relating to a coupling device in the first embodiment above, the disclosure is not limited in this way. For example, according to a fourth embodiment, the coupling device here may be construed as involving an auxiliary device for coupling the adaptor 602 and the connector 404. In this case, the auxiliary device includes the adaptor fixing member 603 and the connector fixing member 405.

The first embodiment described above involves a configuration in which the connector on the catheter device side is structured to have the protruding section and the adaptor on the scanner/pull-back section side is structured to have the inclined end surface and the notched section. However, these configurations of the connector and the adaptor may be reversed so that the adaptor on the scanner/pull-back section side is configured to possess the protruding section and the connector is configured to have the inclined end surface and the notched section. In this case, also, the same effects as above-mentioned can be obtained.

In the embodiments of the coupling device described above and illustrated in the drawing figures, the outer surface of the main body 603 is smooth.

The principles, embodiments and modes of operation of the coupling device and other aspects disclosed here have been described in the foregoing specification, but the invention which is intended to be protected is not to be construed as limited to the particular embodiments disclosed. The embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A coupling device for coupling optical fiber cables, comprising:
    a first fixing member comprised of a wall defining a cylindrical first hollow shape in which a first coupling terminal is disposed, the wall possessing an inner surface, the cylindrical first hollow shape possessing an open end portion at one end of the cylindrical first hollow shape, the cylindrical first hollow shape extending in an axial direction;
    a second fixing member comprised of a wall defining a cylindrical second hollow shape in which a second coupling terminal is disposed, the wall of the second fixing member possessing an outer surface;
    the second fixing member being slidably positionable inside the first fixing member, during which the outer surface of the wall of the second fixing member faces the inner surface of the wall of the first fixing member;
    the first fixing member comprising, at the open end portion, an inclined end surface having an inclination angle which extends toward the open end side in the axial direction of the hollow section, and a notched section extending in the axial direction of the cylindrical first hollow shape, the inclined end surface possessing a distal-most portion and a proximal-most portion, the notched section possessing an open end opening at the inclined end surface at the proximal-most portion;
    the outer surface of the wall of the second fixing member comprising a protruding portion extending in a longitudinal direction of extent of the second fixing member, and
    the inclined end surface possessing spiral shapes with respect to clockwise and counterclockwise circumferential directions, with the open end of the notched section as a center;
    the protruding section of the second fixing member contacting the inclined end surface of the first fixing member during insertion of the second fixing member into the first fixing member, and the protruding section sliding on the inclined end surface to be guided to the notched section in response to urging of the second fixing member further in an insertion direction.

2. The coupling device according to claim 1, wherein the first coupling terminal and the second coupling terminal are coupled with each other by insertion of the protruding section of the second fixing member along the notched section.

3. The coupling device according to claim 1, further comprising a protective cover covering the second fixing member, with the second fixing member being turnable relative to the protective cover.

4. The coupling device according to claim 1, wherein the first fixing member possesses a smooth outer surface.

5. The coupling device according to claim 1, wherein the first fixing member comprises a main body provided with the notched section and possessing an outer surface, the second fixing member also comprising a protective tube possessing an inner surface, the protective tube covering the main body so that the inner surface of the protective tube is in contact with the outer surface of the main body.

6. The coupling device according to claim 1, further comprising a housing in which is housed the main body and the protective tube.

7. An auxiliary device for assisting coupling between terminals of optical fiber cables, comprising:
    a first fixing member comprised of a wall defining a cylindrical first hollow shape, the wall possessing an inner surface, the cylindrical first hollow shape possessing an open end portion at one end of the cylindrical first hollow shape, the cylindrical first hollow shape extending in an axial direction;
    a second fixing member comprised of a wall defining a cylindrical second hollow shape, the wall of the second fixing member possessing an outer surface;
    the second fixing member being slidably positionable inside the first fixing member, during which the outer surface of the wall of the second fixing member faces the inner surface of the wall of the first fixing member;
    the first fixing member comprising, at the open end portion, an inclined end surface having an inclination angle which extends toward the open end side in the axial direction of the hollow section, and a notched section extending in the axial direction of the cylindrical first hollow shape, the inclined end surface possessing a distal-most portion and a proximal-most portion, the notched section possessing an open end opening at the inclined end surface at the proximal-most portion;
    the outer surface of the wall of the second fixing member comprising a protruding portion extending in a longitudinal direction of extent of the second fixing member, and
    the inclined end surface possessing spiral shapes with respect to clockwise and counterclockwise circumferential directions, with the open end of the notched section as a center;
    the protruding section of the second fixing member contacting the inclined end surface of the first fixing member during insertion of the second fixing member into the first fixing member, and the protruding section sliding on the inclined end surface to be guided to the notched section in response to urging of the second fixing member further in an insertion direction.

8. The auxiliary device according to claim 7, further comprising a protective cover covering the second fixing member, with the second fixing member being turnable relative to the protective cover.

* * * * *